United States Patent
Zhou et al.

(10) Patent No.: US 10,060,804 B2
(45) Date of Patent: Aug. 28, 2018

(54) STAGE-TYPE FAST SCANNING CALORIMETRY WHICH CAN BE INTEGRATED WITH OTHER STRUCTURE CHARACTERIZATION APPROACHES

(71) Applicant: Nanjing University, Nanjing, Jiangsu (CN)

(72) Inventors: Dongshan Zhou, Jiangsu (CN); Lai Wei, Jiangsu (CN); Jing Jiang, Jiangsu (CN); Qi Xue, Jiangsu (CN); Wei Chen, Jiangsu (CN); Xiaoliang Wang, Jiangsu (CN); Wei Jiang, Jiangsu (CN); Christoph Schick, Jiangsu (CN)

(73) Assignee: Nanjing University, Nanjing, Jiangsu (CN)

( * ) Notice: Subject to any disclaimer, the term of this patent is extended or adjusted under 35 U.S.C. 154(b) by 253 days.

(21) Appl. No.: 15/028,972

(22) PCT Filed: Dec. 20, 2013

(86) PCT No.: PCT/CN2013/090170
§ 371 (c)(1),
(2) Date: Apr. 13, 2016

(87) PCT Pub. No.: WO2015/058449
PCT Pub. Date: Apr. 30, 2015

(65) Prior Publication Data
US 2016/0238465 A1      Aug. 18, 2016

(30) Foreign Application Priority Data

Oct. 22, 2013  (CN) .......................... 2013 1 0499799

(51) Int. Cl.
*G01K 17/00* (2006.01)
*G01N 25/20* (2006.01)

(52) U.S. Cl.
CPC ........... *G01K 17/006* (2013.01); *G01N 25/20* (2013.01)

(58) Field of Classification Search
CPC ...... G01K 17/006; G01K 17/00; G01K 17/20; G01K 17/08; G01K 19/00; G01N 25/20;
(Continued)

(56) References Cited

U.S. PATENT DOCUMENTS

| | | | | |
|---|---|---|---|---|
| 3,527,081 A * | 9/1970 | Hill | .................. | F02C 7/045 374/11 |
| 4,821,303 A * | 4/1989 | Fawcett | ............... | G01N 23/207 378/71 |
| 5,439,291 A * | 8/1995 | Reading | ................. | B82Y 15/00 374/11 |
| 6,079,873 A * | 6/2000 | Cavicchi | ............ | G01N 25/4866 374/10 |

(Continued)

FOREIGN PATENT DOCUMENTS

| CN | 201060192 | 5/2008 |
|---|---|---|
| CN | 101334398 | 12/2008 |

(Continued)

OTHER PUBLICATIONS

International Search Report of PCT/CN2013/090170 dated Jul. 30, 2014, 4 pages (English and Chinese translations).

*Primary Examiner* — Lisa Caputo
*Assistant Examiner* — Philip Cotey
(74) *Attorney, Agent, or Firm* — Rankin, Hill & Clark LLP

(57) ABSTRACT

A cooling-heating stage-type fast scanning calorimeter capable of being integrated with other microscopic structure characterization techniques. The cooling-heating stage-type fast scanning calorimeter includes a sample chamber provided with light transmission and reflection transparent windows on the walls thereof, a cooling-heating stage provided with internal heating elements and coolant channels for temperature control and also provided with a transmission hole, a sample chamber temperature control system and a fast calorimetric system. The cooling-heating stage-type
(Continued)

fast scanning calorimeter has the advantages that the fast calorimetric system with heating/cooling rates is miniaturized into the cooling-heating stage, and reflection and transmission windows as well as the transmission hole of the cooling-heating stage are used for in-situ integration of calorimetry and microscopic structure characterization; and through program-controlled rapid response, dynamic compensation of sample temperature disturbances caused by incident light in structure measurement is achieved, and sample temperature is stabilized, thus facilitating precise isothermal research.

6 Claims, 3 Drawing Sheets

(58) Field of Classification Search
CPC ........... G01N 25/4806; G01N 25/4826; G01N 25/4833; G01N 25/4846; G01N 25/4853; G01N 25/486; G01N 25/4866
See application file for complete search history.

(56) References Cited

U.S. PATENT DOCUMENTS

| | | | |
|---|---|---|---|
| 7,033,840 B1* | 4/2006 | Tagge | B01L 3/50851 422/51 |
| 2002/0012379 A1* | 1/2002 | Kinoshita | G01N 25/486 374/12 |
| 2002/0146345 A1* | 10/2002 | Neilson | G01N 25/482 422/51 |
| 2007/0133652 A1* | 6/2007 | Siegel | C09D 11/101 374/31 |
| 2012/0201268 A1* | 8/2012 | Boyd | G01K 7/36 374/33 |
| 2013/0121369 A1* | 5/2013 | Thoen | G01K 17/04 374/31 |

FOREIGN PATENT DOCUMENTS

| | | |
|---|---|---|
| CN | 101487806 | 7/2009 |
| CN | 102914558 | 2/2013 |
| EP | 0466226 | 1/1992 |
| WO | 2009149333 | 12/2009 |

* cited by examiner

STAGE-TYPE FAST SCANNING CALORIMETRY WHICH CAN BE INTEGRATED WITH OTHER STRUCTURE CHARACTERIZATION APPROACHES

TECHNICAL FIELD

The present invention relates to the technical field of phase and microstructure analysis equipment, and in particular to a cooling-heating stage-type fast scanning calorimeter capable of being integrated with other microscopic structure characterization techniques, which is analysis equipment capable of achieving fast heat treatment of a sample and in-situ characterization of a microstructure of the sample at the same time.

BACKGROUND

Metastable or transient materials often have unusual physicochemical properties, and many well-performing materials are in a particular metastable state. For example, during steel processing, an austenite is transformed into a metastable martensite through quenching, which greatly improves usability. The structures and properties of metastable materials have always been one of research hotspots, involving various research fields such as materials science, physics, chemistry, biology, energy, pharmacy, food and the environment. At present, the most simple and straightforward way to realize the metastable state of materials is heat treatment. Therefore, thermal analysis, especially fast thermal analysis, has become one of the most effective and reliable means for studying metastable materials.

In recent years, Professor Christoph Schick et al. have used a commercial thin film vacuum sensor (vacuum thermal conductivity gauge, TCG-3880, Xensor Integration, NL) to build the first fast scanning calorimeter (FSC) (Patent No.: US20100046573A1), and the controllable heating/cooling rate of the FSC is 1-10,000 K/s, or even higher. The specific approach is to load a sample of a nanogram to microgram level on the thin film sensor and significantly reduce the sample and additional heat capacity, so as to increase the heating/cooling rate. The method has been used to successfully study the melting-recrystallization-remelting process of many polymers, such as poly(dimethyl phthalate), polypropylene, polyamide blends and isotactic polystyrene. Since such a heating/cooling rate is sufficient to suppress the structural transformation of certain materials, fast scanning calorimetry can be used to study the thermodynamic properties of some metastable materials and also obtain the metastable state of the materials through fast heat treatment. However, the information provided by fast scanning calorimetry is limited and cannot meet the requirement for studying the structures and properties of metastable materials. Therefore, there is a need to develop a technical means which can be used to conduct fast thermal analysis on a sample to obtain the thermal properties of the sample, and at the same time to be integrated with microscopic structure characterization techniques to obtain the structure information of the sample in the metastable state.

There are two difficulties, though, to realize the above technical means. First, the available operation space of most microscopic structure characterization equipment is small, and the available FSC performs temperature control by immersing a vacuum tube in a Dewar flask and in-situ integration with other equipment cannot be achieved; for structure characterization of a metastable material prepared by the FSC, the sample can only be taken out and put into another equipment, and the internal structure of the sample may have changed during this process. Second, since the additional heat capacity of the sample and sensor adopted by the fast scanning calorimeter is small, even low-power incident light can significantly affect the temperature of the sample; however, the available FSC uses power compensation to control the temperature of the sample, and when the incident light used for structure characterization has an effect on the temperature of the sample that exceeds a power compensation limit, the temperature of the sample will be out of control, which may cause the structure of the sample to change.

SUMMARY

In order to overcome the difficulties, a cooling-heating stage-type fast scanning calorimeter is provided. Besides the performances of the FSC, the cooling-heating stage-type fast scanning calorimeter is also characterized in that: first, a transmission window and a reflection window are formed on opposite walls of an airtight sample chamber, a cooling-heating stage provided with heating elements and coolant channels inside is provided, a transmission hole is formed in the cooling-heating stage, and a temperature control system is provided; second, the cooling-heating stage-type fast scanning calorimeter can quickly respond to the change in sample temperature and adjust the sample temperature, and sample temperature control by means of power compensation of the FSC is changed to direct high-speed monitoring of the sample temperature through a program, so as to ensure that the temperature is held steady at a predetermined point and avoid the influence of incident light of structure characterization equipment; third, the cooling-heating stage-type fast scanning calorimeter is placed under a microscope to meet the detection needs of reflection and transmission, and can be integrated with a variety of structure characterization equipment.

The cooling-heating stage-type fast scanning calorimeter comprises a sample chamber (100), a sample chamber temperature control system (400) and a fast calorimetric system (200).

The sample chamber (100) comprises: a cooling-heating stage (110) provided with heating elements and coolant channels inside for temperature control, and also provided with a transmission hole (109), a reflection window (107), a transmission window (108), wiring terminals (101) for thin film sensors, signal line interfaces (102) for the thin film sensors, a coolant inlet (103), a coolant outlet (104), a temperature control signal interface (105) for the cooling-heating stage and an atmosphere channel (106), and the reflection window and transmission window are located on the opposite walls of the airtight sample chamber.

The reflection window (107) allows light to be incident on the sample and exit after reflection. The transmission window (108) allows light to enter, be incident on the sample via the transmission hole (109) and exit through the reflection window (107). Different light-pervious materials are adopted for the reflection window (107) and the transmission window (108) according to different purposes, for example, calcium fluoride lenses can be used for optical detection in ultraviolet, visible and infrared bands, and polyimide film lenses can be used for X-ray related detection.

The cooling-heating stage provides an ambient temperature for the sample.

The surface of the cooling-heating stage is made of pure silver or other materials with good heat conduction, in order to keep the temperature uniformity of the surface of the cooling-heating stage. The cooling-heating stage (110) is internally provided with temperature sensors, heating elements and cooling channels allowing a coolant (such as liquid nitrogen) to pass through; the coolant inlet (103) and the coolant outlet (104) allow the coolant (such as liquid nitrogen) to circulate inside the cooling-heating stage; the transmission hole (109) extends through the cooling-heating stage and is aligned with the reflection window (107) and the transmission window (108), so that light can pass though the cooling-heating stage to be incident on the sample; the wiring terminals (101) for the thin film sensors connect signal lines of the thin film sensors to the signal line interfaces (102) for the thin film sensors; the temperature control signal interface (105) for the cooling-heating stage is connected to the sample chamber temperature control system (400), in order to control the temperature of the cooling-heating stage; and the atmosphere channel (106) allows atmosphere communication inside and outside of the sample chamber.

The sample chamber temperature control system (400) has a heating function as well as a cooling function, so that the surface temperature of the cooling-heating stage is held steady at a predetermined point.

The fast calorimetric system (200) comprises a reference thin film sensor (220), a sample loading thin film sensor (210), a fast temperature control and measurement system (300) and a computer for program control and data processing (500).

The reference thin film sensor (220) and the sample loading thin film sensor (210) must include thermocouples or thermopiles for temperature detection, and heating resistors. Preferably, XEN-39391, XEN-39392, XEN-39394 and XEN-39395 commercial vacuum thermal conductivity gauges with XEA-014 ceramic as substrates manufactured by Xensor Integration from the Netherlands may be used as sensors as needed.

The fast temperature control and measurement system (300) comprises: a PID temperature controller (310) for receiving temperature signals from the reference thin film sensor (220) and producing control signals, a differential amplifier (320) for receiving temperature signals from both the reference sensor (220) and the sample sensor (210) and producing control signals, and a fast digital-analog converter (not shown in the drawings) for signal output and acquisition, wherein the fast digital-analog converter is integrated with the computer (500). The controller (310) provides average heating power for the sample sensor (210) and the reference sensor (220) based on the received temperature signals. The differential amplifier (320) provides compensation power for the sample sensor (210) based on the received temperature signals of the sample sensor (210) and the reference sensor (220). The fast digital-analog converter usually requires one digital-to-analog conversion interface and eight analog-to-digital conversion interfaces, and different sampling rates and precisions are adopted as required. Preferably, the converter adopts an asynchronous sampling rate of 1.25 MS/s or above and a precision of 16 bits or above. At the same time, the converter must have input and output buffers which match the sampling rate. Through the computer (500) or other equipment, a temperature program is written into the output buffer according to a heating/cooling rate, and output to a set port of the controller (310) used for providing the average heating power through digital-analog conversion. The controller (310) is a PID controller, a set end of the controller is connected with a signal output end of the fast digital-analog converter, and a measurement end of the controller is connected with the thermopile of the reference sensor (220). A heating voltage is generated according to signals of the set end and the measurement end, so as to provide the average heating power for the sample sensor (210) and the reference sensor (220). The differential amplifier (320) employs an adder or subtractor composed of an integrated operational amplification circuit, and may also employ a PID controller. The differential amplifier (320) is simultaneously connected to the thermopiles of the sample sensor (210) and the reference sensor (220). A heating compensation voltage is generated based on temperature signals of the two sensors to provide the compensation power for the sample sensor (210).

By the adoption of the cooling-heating stage-type fast scanning calorimeter, calorimetric analysis of a sample can be achieved at a heating/cooling rate as high as 200,000 K/s, under which a sample, especially a polymer sample is subjected to fast heat treatment so as to obtain a certain metastable state thereof. The cooling-heating stage-type fast scanning calorimeter is unique in that, after the metastable sample is obtained, in-situ spectroscopic detection can be conducted on the sample through the reflection window (107), the transmission window (108) and the transmission hole (109), so as to obtain the microstructure information of the sample. Meanwhile, by means of program control, the temperature of the sample can be monitored within milliseconds and held steady at a predetermined point, so as to prevent the incident light from causing the sample to transform due to temperature increase, which may affect test results. Related work cannot be completed on other similar devices (such as the fast scanning calorimeter described in Patent No. US20100046573A1).

BRIEF DESCRIPTION OF THE DRAWINGS

In FIG. 1, 610 represents a light source and detector of structure characterization equipment which can be integrated with the cooling-heating stage-type fast scanning calorimeter; 611 represents a light path of incident light produced by the light source and detector (610) of the structure characterization equipment and reflected light to be received (or transmission light in the case of transmission), and detection light is incident on the surface of the sample from the light source and detector (610) of the structure characterization equipment and is reflected; 620 represents a light source of the structure characterization equipment which can be integrated with the cooling-heating stage-type fast scanning calorimeter; 621 represents a light path of incident light generated by the light source (620) of the structure characterization equipment, which is incident on the sample from the bottom surface of the sample through thin films of the sensors and is transmitted to the light source and detector (610) of the structure characterization equipment to be received. It should be noted that the light source and detector (610) of the structure characterization equipment, the light source (620) of the structure characterization equipment and the light paths (611) and (621) are not included in the present invention and are only used to illustrate the present invention.

In FIG. 2, 100 represents the sample chamber, 110 represents the cooling-heating stage in the sample chamber (100), 101 represents wiring terminals for the thin film sensors, 102 represents signal wire interfaces for the thin film sensors, 103 represents a coolant inlet, 104 represents a coolant outlet, 105 represents a temperature control signal interface for the cooling-heating stage, 106 represents an atmosphere channel in the sample chamber, 210 represents the sample loading thin film sensor, 214 represents a wire for signal transmission of the sample sensor (210), 220 represents the reference thin film sensor, 224 represents a wire for signal transmission of the reference sensor (220), and 107 represents the reflection window. It should be noted that the reflection window (107) is located above the sectional view, and is only used to explain its location here.

In FIG. 3, 100 represents the sample chamber, 101 represents the wiring terminals for the thin film sensors, 107 represents the reflection window, 108 represents the transmission window, 110 represents the cooling-heating stage, 109 represents the transmission hole extending through the cooling-heating stage, 210 represents the sample loading thin film sensor, and 214 represents a wire for signal transmission of the sample sensor (210).

In FIG. 4, 110 represents the cooling-heating stage, 210 represents the sample loading thin film sensor, 220 represents the reference thin film sensor, 310 represents a PID temperature controller, 320 represents a differential amplifier, 211 represents a signal line of a thermopile of the sample sensor (210), 212 represents a signal line of the PID temperature controller (310) loading average heating power for the sample sensor (210), 213 represents a signal line of the differential amplifier (320) loading compensation power for the sample sensor (210), 221 represents a signal line of a thermopile of the reference sensor (220), and 222 represents a signal line of the PID temperature controller (310) loading average heating power for the reference sensor (220).

DETAILED DESCRIPTION OF THE INVENTION

The specific embodiments of the present invention will be further described in detail with reference to the accompanying drawings. The following example is used to illustrate the present invention but is not intended to limit the scope of the present invention.

Figure 1:
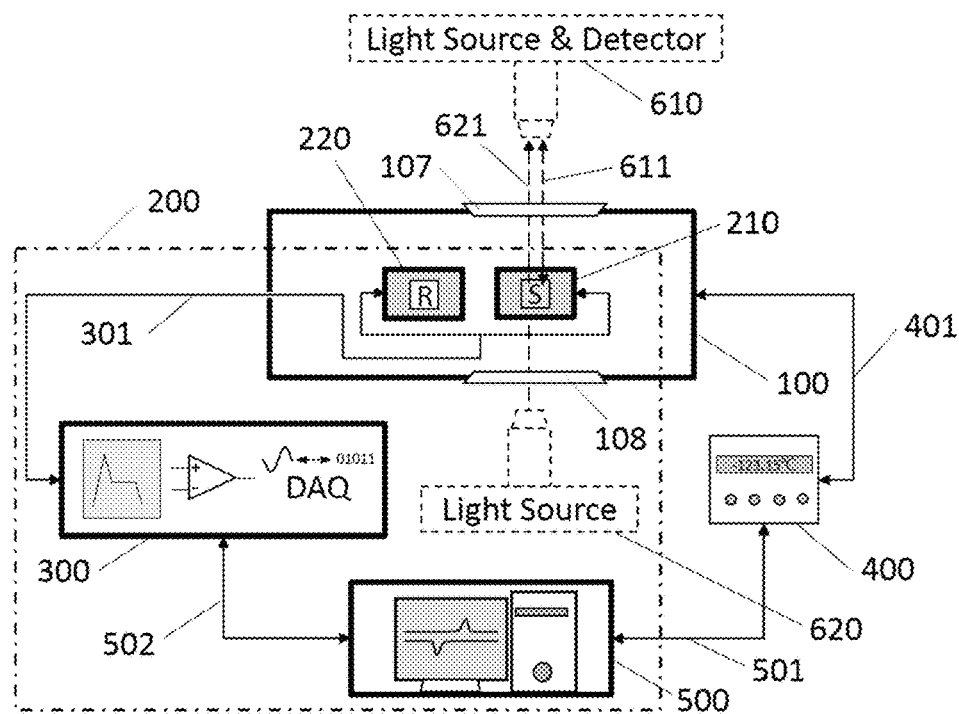
FIG. 1 is a modular structure chart of a cooling-heating stage-type fast scanning calorimeter according to the present invention, wherein 100 represents a sample chamber, 107 represents a reflection window located on the upper surface of the sample chamber (100), 108 represents a transmission window located on the lower surface of the sample chamber (100), 200 represents a fast calorimetric system, 210 represents a sample loading thin film sensor, 220 represents a reference thin film sensor, 300 represents a fast temperature control and measurement system, 301 represents a signal transmission line of the thin film sensors, 400 represents a sample chamber temperature control system used for controlling the surface temperature of the cooling-heating stage in the sample chamber, 401 represents a temperature control signal line for the sample chamber, 500 represents a computer (provided with a fast digital-analog converter inside) for program control and data processing, 501 represents a data transmission line between the computer (500) and the sample chamber temperature control system (400), and 502 represents a data transmission line between the computer (500) and the fast temperature control and measurement system (300).

FIG. 1 is a modular structure chart of a cooling-heating stage-type fast scanning calorimeter according to the example of the present invention. The sample loading thin film sensor (210) and the reference thin film sensor (220) are placed on the surface of the cooling-heating stage (110) in the sample chamber (100) (see FIG. 2), and the ambient temperatures of the two thin film sensors (210 and 220) are controlled by the sample chamber temperature control system (400). The fast temperature control and measurement system (300) controls and acquires the temperatures of heating areas of the two thin film sensors (210 and 220) according to a temperature program set value of the computer (500) based on the ambient temperatures provided by the cooling-heating stage (110), and transmits corresponding data to the computer (500) for subsequent calculation and processing, and the data includes the thermodynamic information of the sample during the temperature program.

The sample chamber temperature control system (400) controls and measures the ambient temperatures of the two thin film sensors (210 and 220). Temperature measurement and heating elements are arranged inside the cooling-heating stage (110). The sample chamber temperature control system (400) obtains the surface temperature of the cooling-heating stage (110) through the temperature control signal interface (105) for the cooling-heating stage, and generates heating and cooling signals according to the temperature. The heating signal is loaded to the heating element in the cooling-heating stage through the interface (105), and the cooling signal controls an external liquid nitrogen pump or solenoid valve and the like. A coolant (such as liquid nitrogen) enters the cooling-heating stage for circulation through a coolant inlet (103) and is discharged through a coolant outlet (104). The sample chamber temperature control system (400) controls the surface temperature of the cooling-heating stage in the above manner. In addition, 106 is an atmosphere channel which allows communication inside and outside of the sample chamber and can be used to control the atmosphere in the sample chamber, so as to prevent the atmosphere from affecting the sample.

Figure 2:
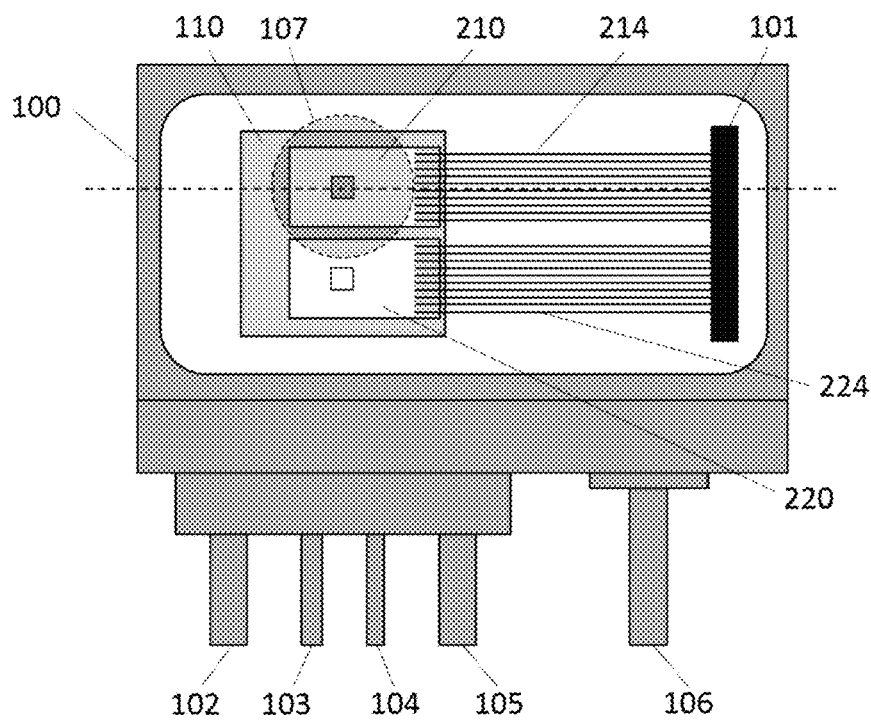
FIG. 2 is a top sectional view of the sample chamber of the cooling-heating stage-type fast scanning calorimeter according to the present invention, and the profile position is shown by dotted line in FIG. 3.

The sample loading thin film sensor (210) and the reference thin film sensor (220) shown in FIG. 2 have thin film heating areas, and heating resistors and thermopiles for measuring the temperatures of the heating areas are arranged around the heating areas. The temperature difference between the heating areas (namely hot end) and the ambient temperature (namely cold end) is obtained through the thermopiles, and by referring to the surface temperature of the cooling-heating stage (generally considered to be equal to the ambient temperature), the temperature of the heating area of each sensor can be calculated. The temperature signals and the heating signals of the two sensors are connected to the wiring terminals (101) via wires (214 and 224) and come out of the sample chamber via interfaces (102).

Figure 4:
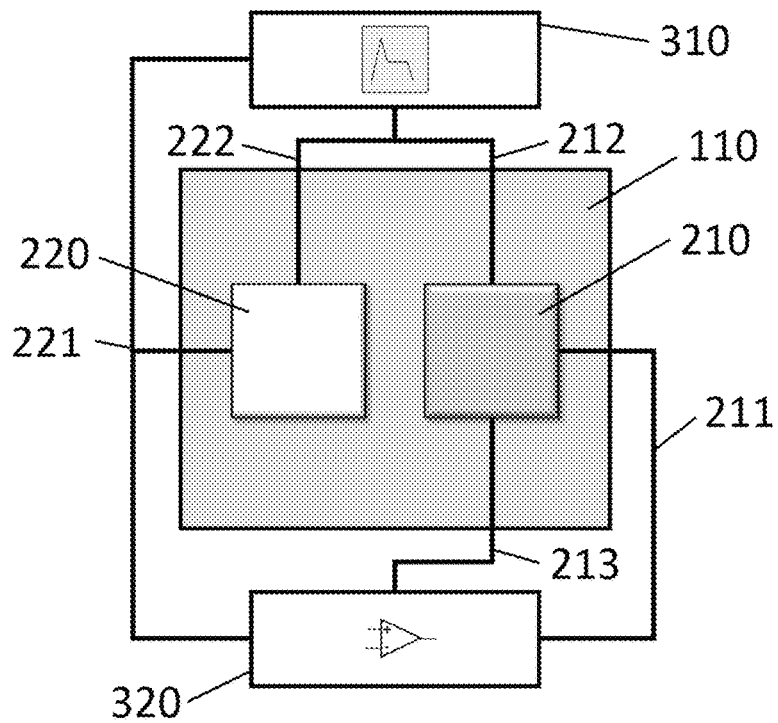
FIG. 4 is a modular structure chart of the fast temperature control and measurement system (300) of the cooling-heating stage-type fast scanning calorimeter according to the present invention.

A PID temperature controller (310) shown in FIG. 4 obtains the temperature of the heating area of the reference sensor (220) via a temperature signal line (221), and provides average heating power to the reference sensor (220) and the sample sensor (210) simultaneously according to a program set value and the measured temperature of the heating area of the reference sensor (220). A differential amplifier (320) provides compensation power for the sample sensor (210) based on the measured temperatures of the heating areas of the reference sensor (220) and the sample sensor (210), so as to keep the temperatures of the heating areas of the sample sensor (210) and the reference sensor (220) equal. In the above process, the surface temperature of the cooling-heating stage (110) is constant, in other words, constant temperature of the cold end of each sensor is equivalently ensured.

Figure 3:
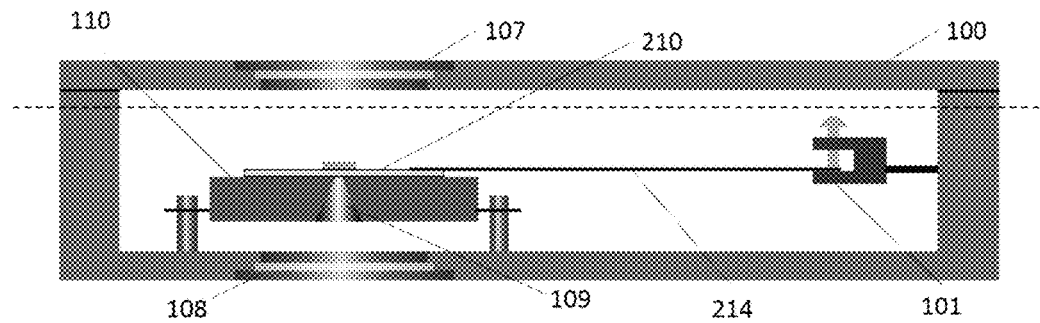
FIG. 3 is a side sectional view of the sample chamber of the cooling-heating stage-type fast scanning calorimeter according to the present invention, and the profile position is shown by dotted line in FIG. 2.

The reflection window (107), the transmission window (108) and the transmission hole (109) shown in FIG. 3 are opposite the heating area of the sample sensor (210). Different materials can be adopted for the reflection window (107) and the transmission window (108) according to specific needs (such as the refractive index and transmittance to a certain light source), for example, calcium fluoride lenses can be used for optical detection in ultraviolet, visible and infrared bands, and polyimide film lenses can be used for X-ray related detection. When the cooling-heating stage-type fast scanning calorimeter is integrated with a spectroscopic method, if reflected light needs to be detected, incident light is made to be incident on the surface of the sample and reflected through the reflection window (107) for detection; if transmission light needs to be detected, incident light can be made to be incident on the sample through the transmission window (108) and the transmission hole (109), and transmission light is emitted through the reflection window (107) for detection.

According to the layout shown in FIG. 2 and FIG. 3, the cooling-heating stage type sample chamber (100) can be dimensioned to be 170 mm in length, 108 mm in width and 30.34 mm in height, or even smaller. Therefore, the cooling-heating stage-type fast scanning calorimeter can be conveniently and effectively integrated with a variety of microscopic structure characterization equipment, including optical microscopy, micro-Raman spectrometer and X-ray transmitter.

Figure 5:
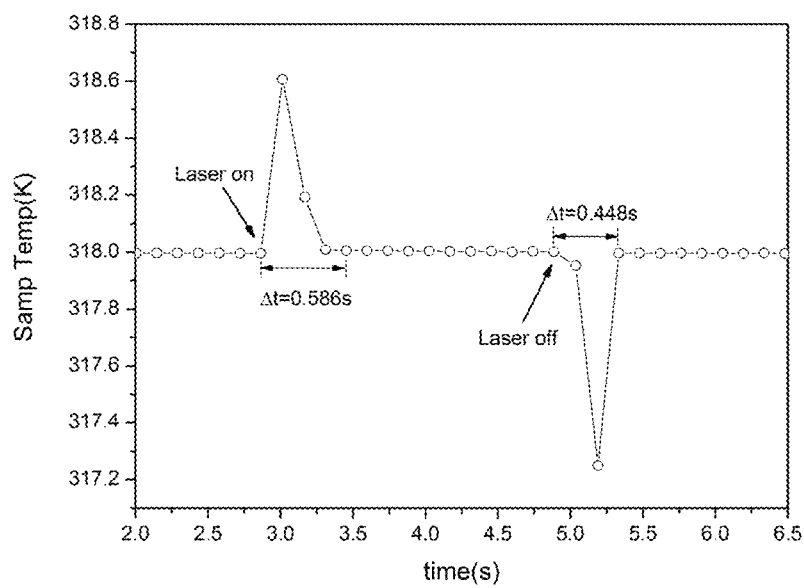
FIG. 5 shows the effect of Raman laser on the temperature of the sample when it is incident on the sample and is removed, as well as a graphical result of temperature control of the cooling-heating stage-type fast scanning calorimeter.

In order to avoid the effect of external detection light on the sample temperature, the sample temperature is obtained by calculation using signals acquired by a fast temperature control and measurement system (300), and the temperature is detected by a computer (500) in real time by means of program control, and regulated by the fast temperature control and measurement system (300) within milliseconds, so as to stay at a set value. In order to verify the effect of light on the temperature of the sample to be tested, polyethylene terephthalate (PET) is used as the sample and subjected to an irradiation enabling and disenabling experiment using a laser source with a sample-area laser energy level of 6 mW and a wavelength of 785 nm at 320 K, and the temperature of the sample during the process is shown in FIG. 5. It can be seen from the figure that whether laser light is suddenly turned on or off, the effect of the light source on the temperature of the sample is less than ±0.8 K, and the sample temperature can be adjusted to the set value within a time period of not more than 0.6 s.

In addition, in order to ensure the reliability of detection results when the cooling-heating stage-type fast scanning calorimeter is integrated with the microscopic structure characterization equipment, the following experimental schemes are suggested: first, set a temperature program by means of the cooling-heating stage-type fast scanning calorimeter for heat treatment of the sample, so as to obtain a sample in a desired state; second, cool the sample to a temperature much lower than the temperature for structural transformation at a cooling rate which can suppress the structure change of the sample (except for glass transition) and keep the temperature unchanged; and third, conduct structure characterization on the sample using the microscopic structure characterization equipment integrated with the cooling-heating stage-type fast scanning calorimeter.

The above embodiments are only used to illustrate the present invention, and are not intended to limit the present invention. Those skilled in the related art may make various changes and modifications without departing from the spirit and scope of the present invention. Therefore, all equivalent technical solutions also belong to the scope of the present invention, and the scope of patent protection of the present invention should be defined by the claims.

What is claimed is:

1. A cooling-heating platform-type fast scanning calorimeter capable of being integrated with microscopic structure characterization techniques, comprising:
    a sample chamber including a reflection window and a transmission window, wherein the reflection window and the transmission window are arranged on opposite walls of the sample chamber;
    a cooling-heating platform arranged in the sample chamber upon which a sample is arranged, and including internal temperature sensors, internal heating elements and internal coolant channels, the temperature sensors monitoring a surface temperature of a surface of the cooling-heating platform, and the heating elements and the coolant channels controlling the surface temperature controlling, and
    a transmission hole extending through the cooling-heating platform;
    a sample chamber temperature control system in communication with the temperature sensors, the heating elements and the coolant channels, for measuring and controlling the surface temperature,
    a fast calorimetric system including thin film sensors arranged on the surface of the cooling-heating platform.

2. The cooling-heating platform-type fast scanning calorimeter of claim 1, wherein the sample chamber further comprises:
    wiring terminals connected to the thin film sensors via signal lines, the wiring terminals also being connected to signal line interfaces through which temperature signals from the thin film sensors exit the sample chamber,
    a coolant inlet connected the coolant channels and through which a coolant enters the sample chamber and into the coolant channels,
    a coolant outlet connected to the coolant channels and through which the coolant exits the sample chamber and from the coolant channels,
    a temperature control signal interface through which temperature signals from the temperature sensors exit the sample chamber, and
    an atmosphere channel providing communication between an atmosphere inside of the sample chamber and an atmosphere outside of the sample chamber.

3. The cooling-heating platform-type fast scanning calorimeter of claim 1, wherein the sample chamber temperature control system has a heating function as well as a cooling function, so that the surface temperature of the cooling-heating platform is held steady at a predetermined point.

4. The cooling-heating platform-type fast scanning calorimeter of claim 1, wherein:

the thin film sensors are arranged on the surface of the cooling-heating platform, and comprise temperature sensors and heating elements, the thin film sensors comprise a reference thin film sensor, and a sample loading thin film sensor, the fast calorimetric system further comprises a fast temperature control and measurement system, and a computer for program control and data processing, the fast temperature control and measurement system comprises:
- a PID temperature controller for receiving temperature signals from the reference thin film sensor, and producing control signals for an average heating power to the sample loading thin film sensor and the reference thin film sensor,
- a differential amplifier for receiving temperature signals from both the reference thin film sensor and the sample loading thin film sensor, and producing control signals for providing compensation power for the sample loading thin film sensor to keep a temperature of the sample loading thin film sensor equal to a temperature of the reference thin film sensor, and
- a fast digital-analog converter for signal output and acquisition, and the fast digital-analog converter is connect to the computer.

5. The cooling-heating platform-type fast scanning calorimeter of claim 2, wherein:
- the thermal cooling-heating platform provides an ambient temperature for the sample,
- the surface of the cooling-heating platform comprises high heat conductive material,
- the transmission hole is aligned with the reflection window and the transmission window so that light can pass though the cooling-heating platform to be incident on the sample;
- the temperature control signal interface is connected to the sample chamber temperature control system; and
- the sample chamber temperature control system is connected to the computer.

6. The cooling-heating platform-type fast scanning calorimeter of claim 4, wherein the temperature sensors of the thin film sensors include thermocouples or thermopiles for temperature detection, and the heating elements of the thin film sensors include heating resistors.

* * * * *